(12) United States Patent
Burks

(10) Patent No.: US 7,215,989 B1
(45) Date of Patent: May 8, 2007

(54) MULTIPLE ELECTRODE ASSEMBLY

(76) Inventor: Jonathan W. Burks, 825 S. Dickerson Rd., Goodlettsville, TN (US) 37072

( * ) Notice: Subject to any disclaimer, the term of this patent is extended or adjusted under 35 U.S.C. 154(b) by 53 days.

(21) Appl. No.: 10/800,438

(22) Filed: Mar. 15, 2004

(51) Int. Cl.
*A61B 5/04* (2006.01)
(52) U.S. Cl. .................. 600/393; 600/391; 600/392
(58) Field of Classification Search ............. 600/393
See application file for complete search history.

(56) References Cited

U.S. PATENT DOCUMENTS

| | | | | |
|---|---|---|---|---|
| 4,233,987 A | * | 11/1980 | Feingold | ............... 600/382 |
| 4,687,004 A | | 8/1987 | Zenkich | |
| 4,777,954 A | * | 10/1988 | Keusch et al. | ............. 600/392 |
| 5,255,677 A | * | 10/1993 | Schaefer et al. | ............ 600/384 |
| 5,445,537 A | * | 8/1995 | Abyzov | ................... 600/397 |
| 5,678,545 A | | 10/1997 | Stratbucker | |
| 5,868,671 A | | 2/1999 | Mahoney | |
| 6,006,125 A | | 12/1999 | Kelly et al. | |
| D429,337 S | | 8/2000 | Sanfilippo | |
| 6,134,480 A | | 10/2000 | Minogue | |
| 6,711,427 B1 | * | 3/2004 | Ketelhohn | ................ 600/372 |

\* cited by examiner

*Primary Examiner*—Lee S. Cohen

(57) ABSTRACT

Multiple electrode assemblies provide an electrical connection between a patient's body and monitoring equipment. A multiple electrode assembly requires only half as many assemblies as a conventional single electrode assembly to attach a patient to multiple pieces of equipment. Less time is required to attach the patient to the monitoring equipment. There is less patient discomfort since fewer assemblies are attached to the patient. The placement of fewer assemblies also leads to a reduced cost. The assemblies can take on a number of different shapes and lead attachment configurations to accommodate a wide range of monitoring functions.

10 Claims, 4 Drawing Sheets

MULTIPLE ELECTRODE ASSEMBLY

BACKGROUND OF THE INVENTION

1. Field of the Invention

The present invention relates to a multiple electrode assembly for use in connection with EKG machines. The multiple electrode assembly has particular utility in connection with bioelectric monitoring.

2. Description of the Prior Art

Multiple electrode assemblies are desirable for providing an electrical connection between a patient's body and monitoring equipment such as an EKG machine. A multiple electrode assembly, as opposed to a single electrode assembly, is attractive for a number of reasons. Only half as many assemblies are required to attach a patient to multiple pieces of equipment. This means that less time is required in an emergency situation to attach the patient to the monitoring equipment. There is less patient discomfort since fewer assemblies are attached to the patient. The placement of fewer assemblies also leads to a reduced cost.

The use of adhesive multiple electrode systems is known in the prior art. For example, U.S. Pat. No. 6,134,480 to Minogue discloses an electrode assembly. However, the Minogue '480 patent does not have an electrical isolation perforation, and has further drawbacks of lacking an electrical isolation slit.

U.S. Pat. No. 5,678,545 to Stratbucker discloses an anisotropic adhesive multiple electrode system, and method of use that provides a bioelectric interface. However, the Stratbucker '545 patent does not have an electrical isolation perforation.

Similarly, U.S. Pat. No. 4,687,004 to Zenkich discloses a dual element electrical connector that produces an electrical connection with a body. However, the Zenkich '004 patent can not be used without the additional circuitry required for a test mode and a variable resistor, nor can it be manufactured as inexpensively because of its additional complications of circuitry for a test mode and a variable resistor.

In addition, U.S. Pat. No. 6,006,125 to Kelley et al. discloses a universal electric cardiogram sensor positioning device and method that positions sensors on the human torso. However, the Kelly et al. '125 patent does not allow the user to place only one sensor, and has the additional deficiency of being limited to usage only in electrocardiograms.

Furthermore, U.S. Pat. No. 5,868,671 to Mahoney discloses a multiple ECG electrode strip that connects an ECG measuring device to a patient. However, the Mahoney '671 patent does not allow the user to place only one electrode, and has the additional deficiency of not having multiple electrodes per pad.

Lastly, United States Pat. No. Des. 429,337 to Sanfilippo discloses an electrode that connects an electrical device to a body. However, the Sanfilippo '337 patent does not have an electrical isolation perforation, and also lacks an electrical isolation slit.

While the above-described devices fulfill their respective, particular objectives and requirements, the aforementioned patents do not describe a multiple electrode assembly that allows bioelectric monitoring. The Minogue '480 patent, the Stratbucker '545 patent, and the Sanfilippo '337 patent make no provision for an electrical isolation perforation. The Kelly et al. '125 patent and the Mahoney '671 patent do not allow the user to place only one electrode. Finally, the Zenkich '004 patent cannot be used without the additional circuitry required for a test mode and a variable resistor, rendering it more expensive to manufacture and more complex to use.

Therefore, a need exists for a new and improved multiple electrode assembly that can be used for bioelectric monitoring. In this regard, the present invention substantially fulfills this need. In this respect, the multiple electrode assembly according to the present invention substantially departs from the conventional concepts and designs of the prior art, and in doing so provides an apparatus primarily developed for the purpose of bioelectric monitoring.

SUMMARY OF THE INVENTION

In view of the foregoing disadvantages inherent in the known types of adhesive multiple electrode systems now present in the prior art, the present invention provides an improved multiple electrode assembly, and overcomes the above-mentioned disadvantages and drawbacks of the prior art. As such, the general purpose of the present invention, which will be described subsequently in greater detail, is to provide a new and improved multiple electrode assembly for bioelectric monitoring which has all the advantages of the prior art mentioned heretofore and many novel features that result in a multiple electrode assembly which is not anticipated, rendered obvious, suggested, or even implied by the prior art, either alone or in any combination thereof.

To attain this, the present invention essentially comprises a body made of a nonconducting flexible material. Cut into the body are a plurality of insertion holes. Inserted into each insertion hole is a lead attachment made of a conducting material such as metal. Also, a skin attachment is attached to the underside of the body.

There has thus been outlined, rather broadly, the more important features of the invention in order that the detailed description thereof that follows may be better understood and in order that the present contribution to the art may be better appreciated.

The invention may also include an electrically conductive adhesive as the skin attachment. Also, an electrical isolation perforation or an electrical isolation slit may be present in the body. A removable peel off backing with a peel tab to facilitate the removal process may also be present to protect the conductive adhesive when the invention is not in use. The lead attachment may further comprise a lead insertion which is inserted through each insertion hole and a wire which is connected at one end to the lead insertion and that the other end to a lead connector. Finally, the body may assume other shapes in addition to circular such as rectangular or bone-shaped. There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently current, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved multiple electrode assembly that has all of the advantages of the prior art adhesive multiple electrode systems and none of the disadvantages.

It is another object of the present invention to provide a new and improved multiple electrode assembly that may be easily and efficiently manufactured and marketed.

An even further object of the present invention is to provide a new and improved multiple electrode assembly that has a low cost of manufacture with regard to both materials and labor, and which accordingly is then susceptible of low prices of sale to the consuming public, thereby making such multiple electrode assembly economically available to the buying public.

Still another object of the present invention is to provide a new multiple electrode assembly that provides in the apparatuses and methods of the prior art some of the advantages thereof, while simultaneously overcoming some of the disadvantages normally associated therewith.

Even still another object of the present invention is to provide a multiple electrode assembly for bioelectric monitoring. This allows the user to connect a patient to multiple pieces of equipment using only half as many assemblies as would normally be required.

Still yet another object of the present invention is to provide a multiple electrode assembly for bioelectric monitoring. This makes it possible to more rapidly attach the patient to multiple pieces of equipment, which is particularly important in an emergency situation.

A further object of the present invention is to provide a multiple electrode assembly for bioelectric monitoring. This enables the patient to experience less discomfort since fewer assemblies are attached to the patient.

A still further object of the present invention is to provide a multiple electrode assembly for bioelectric monitoring. This allows the attachment of a patient to multiple monitoring machines at a reduced cost since fewer assemblies are used than would ordinarily be required.

Lastly, it is an object of the present invention to provide a new and improved multiple electrode assembly for bioelectric monitoring.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated current embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DESCRIPTION OF THE CURRENT EMBODIMENT

Figure 1:
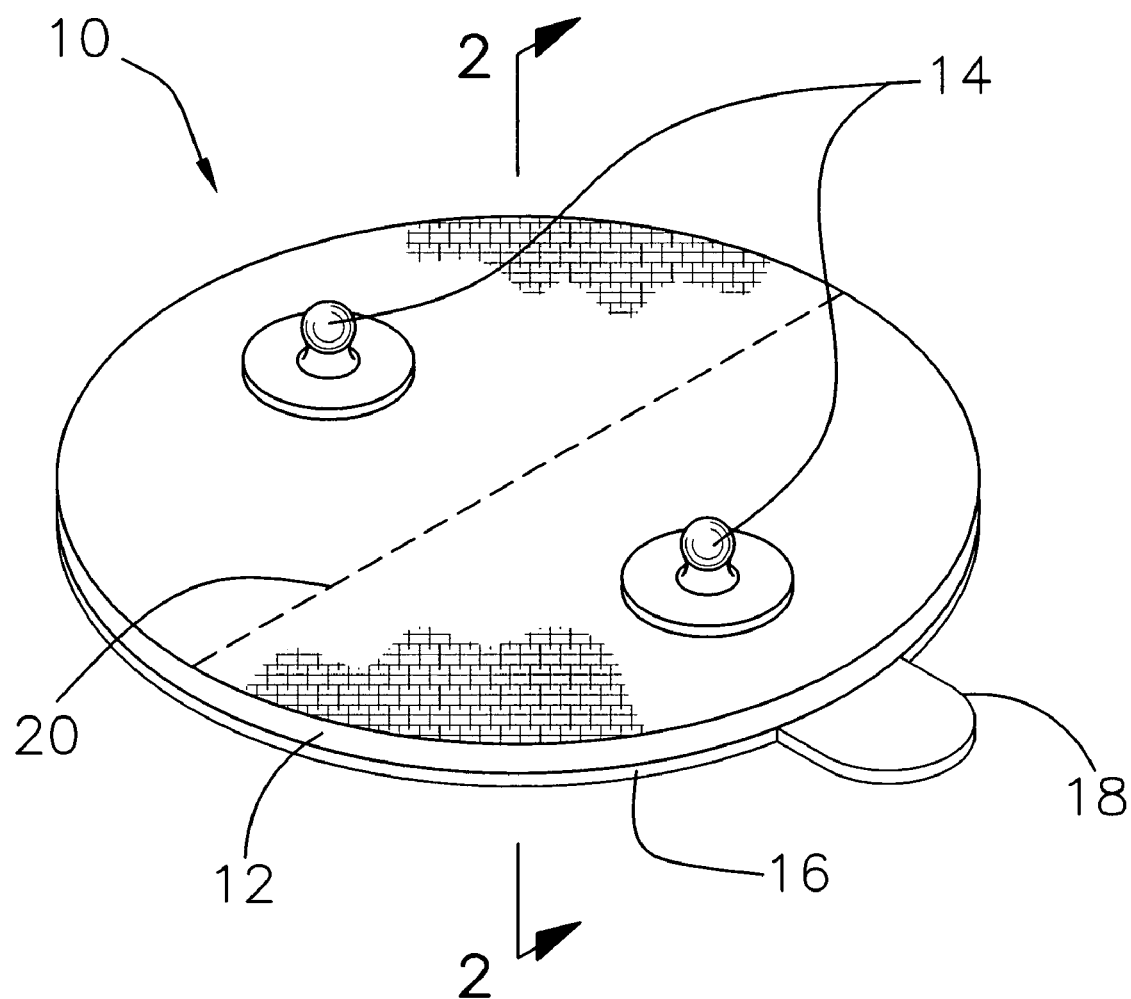
FIG. 1 is a top perspective view of the current embodiment of the multiple electrode assembly constructed in accordance with the principles of the present invention.

Referring now to the drawings, and particularly to FIGS. 1–5, a current embodiment of the multiple electrode assembly of the present invention is shown and generally designated by the reference numeral 10.

In FIG. 1, a new and improved multiple electrode assembly 10 of the present invention for bioelectric monitoring is illustrated and will be described. More particularly, the multiple electrode assembly 10 has a circular body 12 with a diameter of 2¼ inches made of a flexible, nonconducting material such as rubber. Inserted through body 12 are lead attachments 14 made of a conductive material such as metal. Removably attached to the underside of body 12 is peel-off backing 16 with peel tab 18 to facilitate the removal process. Electrical isolation perforation 20, which bisects body 12, also is visible.

Figure 2:
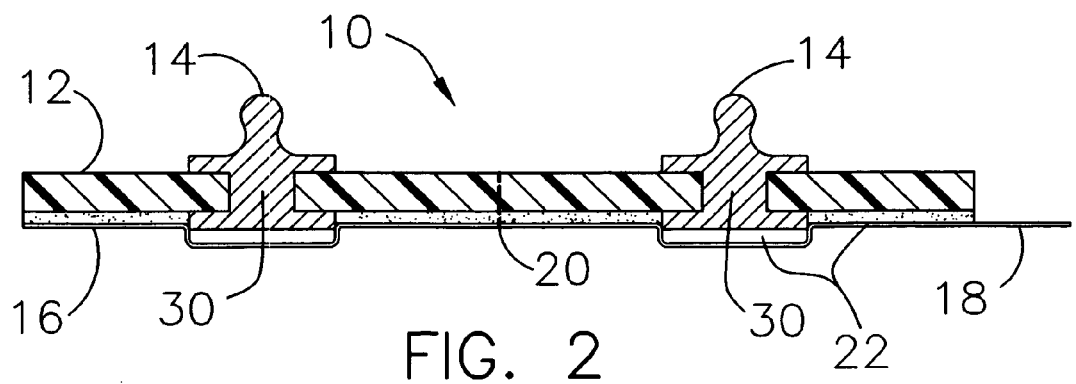
FIG. 2 is a side sectional view of the multiple electrode assembly of the present invention.

Moving on to FIG. 2, a new and improved multiple electrode assembly 10 of the present invention for bioelectric monitoring is illustrated and will be described. More particularly, the multiple electrode assembly 10 has a body 12 with insertion holes 30 cut in it. Lead attachments 14 are inserted through the insertion holes 30. Electrically conductive adhesive 22 is attached to the undersides of body 12 and lead attachments 14. Covering electrically conductive adhesive 22 is peel-off backing 16 with peel tab 18 attached. Electrical isolation perforation 20, which bisects the body 12, is also shown.

Figure 3:
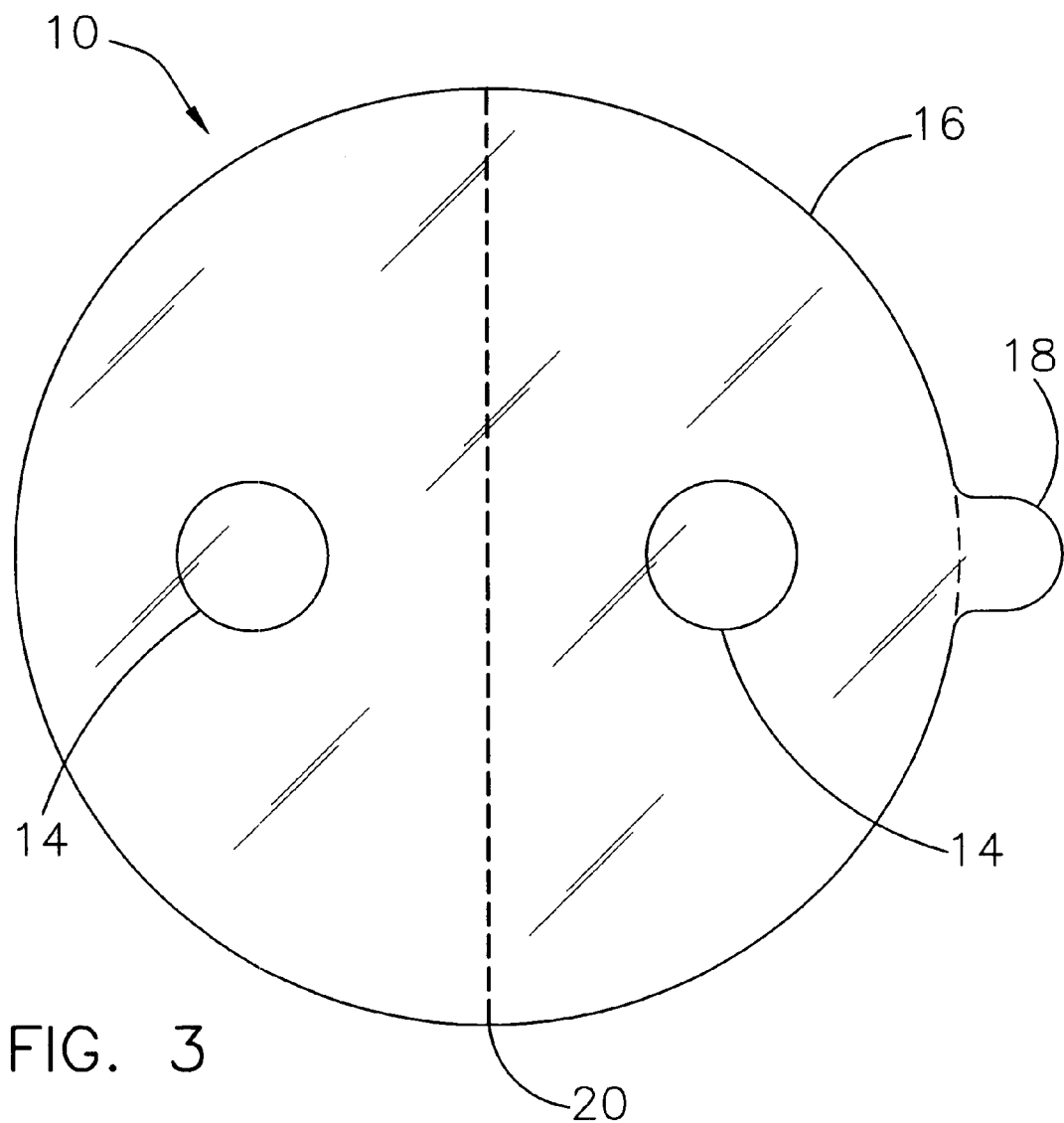
FIG. 3 is a bottom side sectional view of the multiple electrode assembly of the present invention.

Continuing with FIG. 3, a new and improved multiple electrode assembly 10 of the present invention for bioelectric monitoring is illustrated and will be described. More particularly, the multiple electrode assembly 10 has a peel-off backing 16 with peel tab 18 shown. The underside of lead attachments 14 are visible through peel-off backing 16. Electrical isolation perforation 20 is also shown behind peel-off backing 16.

Figure 4:
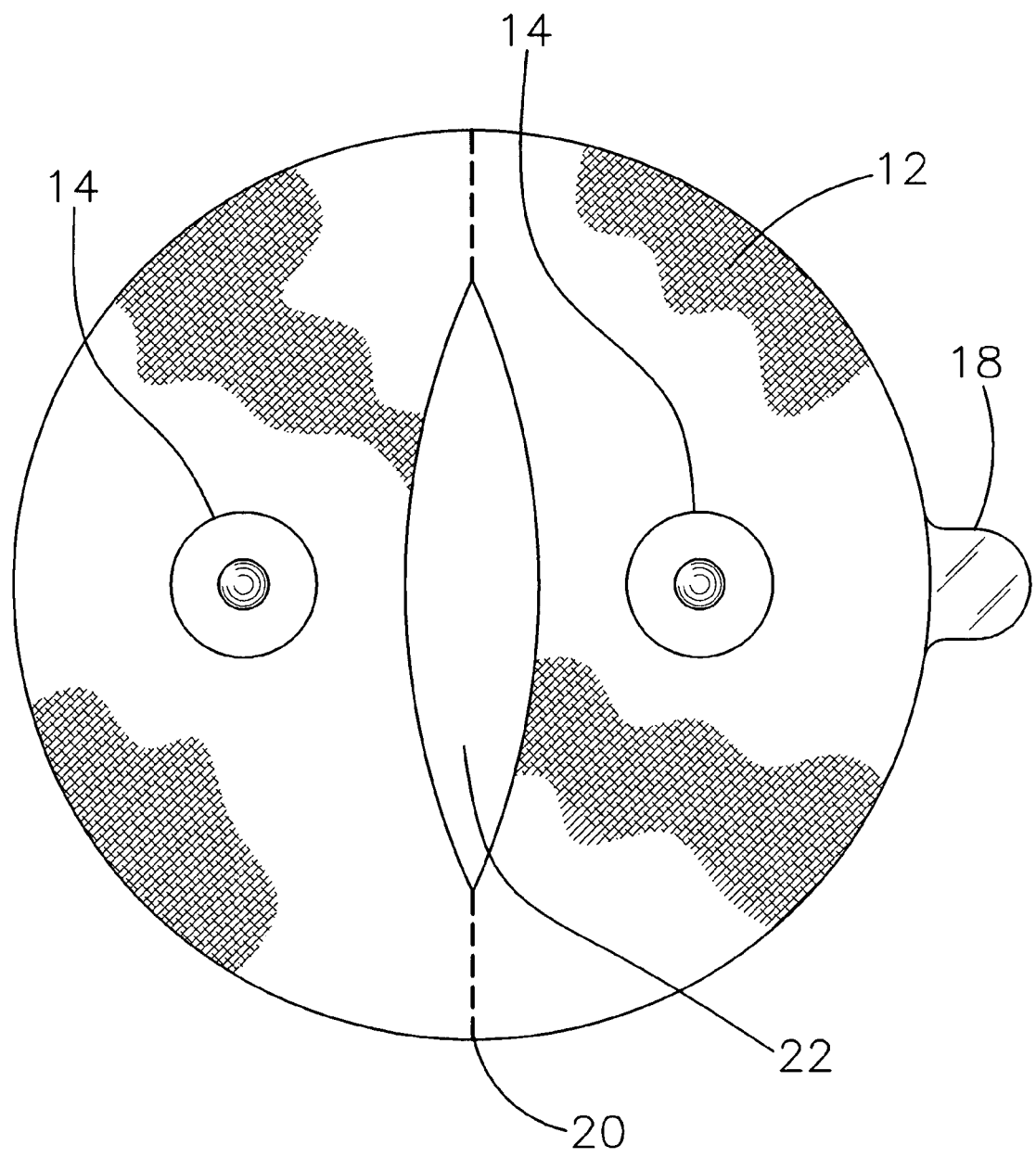
FIG. 4 is a top side view of the multiple electrode assembly of the present invention.

Furthermore, FIG. 4, a new and improved multiple electrode assembly 10 of the present invention for bioelectric monitoring is illustrated and will be described. More particularly, the multiple electrode assembly 10 has a body 12 with lead attachments 14 inserted through it. Peel tab 18 is shown. Also visible are electrical isolation slit 22 in the center of body 12. Electrical isolation perforation 20 is also shown bisecting the portion of body 12 not already separated by electrical isolation slit 22.

Figure 5:
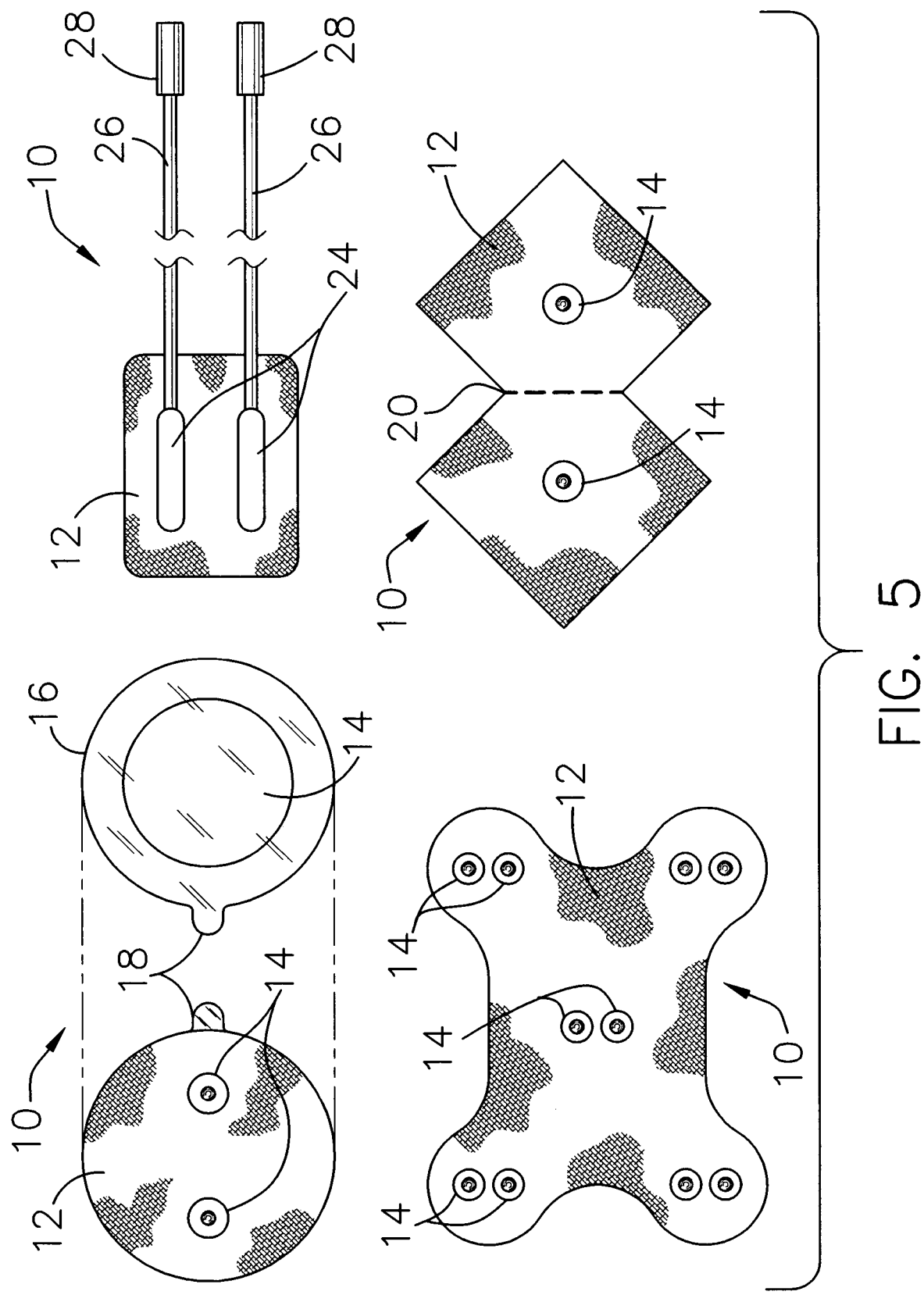
FIG. 5 is a top side view of the multiple electrode assembly of the present invention.

Concluding with FIG. 5, a new and improved multiple electrode assembly 10 of the present invention for bioelectric monitoring is illustrated and will be described. More particularly, the multiple electrode assembly 10 has a body 12 with lead attachments 14, peel-off backing 16, and peel tab 18. Several alternative shapes for the body and placements and quantities of lead attachments are shown. An example of electrical isolation perforation 20 is visible. An alternative embodiment of the lead attachments is also shown wherein the lead attachments comprise lead inserts 24, wires 26, and lead connectors 28.

While a current embodiment of the multiple electrode assembly has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable nonconducting, flexible material such as plastic or fabric may be used instead of the rubber body described. Also, the metal lead attachments could be made of any conducting material such as metal-coated plastic. Furthermore, a wide variety of body shapes can be used in addition to the circular shape described.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A multiple electrode assembly for bioelectric monitoring comprising:
    a body having a top surface, a bottom surface, an outer edge, and a middle;
    an electrical isolation slit having opposing ends, wherein said middle of said body defines a slit therein to comprise said electrical isolation slit;
    a plurality of electrical isolation perforations having opposing ends, wherein said electrical isolation perforations extend from said opposing ends of said electrical isolation slit to said outer edge of said body, and wherein said electrical isolation perforations and said electrical isolation slit combine to bisect said body;
    a plurality of insertion holes in said body wherein said body comprises a plurality of holes therein to comprise said insertion holes, said insertion holes being placed in said body in pairs;
    a plurality of lead attachments inserted through said insertion holes; and
    a skin attachment attached to said bottom surface of said body.

2. The multiple electrode assembly as defined in claim 1, wherein said body is selected from the group consisting of plastic, rubber, and fabric.

3. The multiple electrode assembly as defined in claim 1, wherein said lead attachments are selected from the group consisting of steel, copper, aluminum, and metal-coated plastic.

4. The multiple electrode assembly as defined in claim 1, wherein said skin attachment is an electrically conductive adhesive.

5. The multiple electrode assembly as defined in claim 1, further comprising a peel-off backing with a side removably attached to said bottom surface of said body.

6. The multiple electrode assembly as defined in claim 5, further comprising a peel tab attached to said side of said peel-off backing.

7. The multiple electrode assembly as defined in claim 1, wherein said body is circular in shape.

8. The multiple electrode assembly as defined in claim 1, wherein said lead attachments are nipple shaped.

9. A multiple electrode assembly for bioelectric monitoring comprising:
    a body having a top surface, a bottom surface, an outer edge, and a middle;
    an electrical isolation slit having opposing ends, wherein said middle of said body defines a slit therein to comprise said electrical isolation slit;
    a plurality of electrical isolation perforations having opposing ends, wherein said electrical isolation perforations extend from said opposing ends of said electrical isolation slit to said outer edge of said body, and wherein said electrical isolation perforations and said electrical isolation slit combine to bisect said body;
    a plurality of insertion holes in said body wherein said body comprises a plurality of holes therein to comprise said insertion holes, said insertion holes being placed in said body in pairs;
    a plurality of lead attachments inserted through said insertion holes;
    an electrically conductive adhesive attached to said bottom surface of said body; and
    a peel-off backing with a side removably attached to said bottom surface of said body.

10. The multiple electrode assembly as defined in claim 9, further comprising a peel tab attached to said side of said peel-off backing.

* * * * *